May 19, 1942. R. L. BYRUM Plant Pat. 517
ROSE PLANT
Filed Nov. 1, 1941
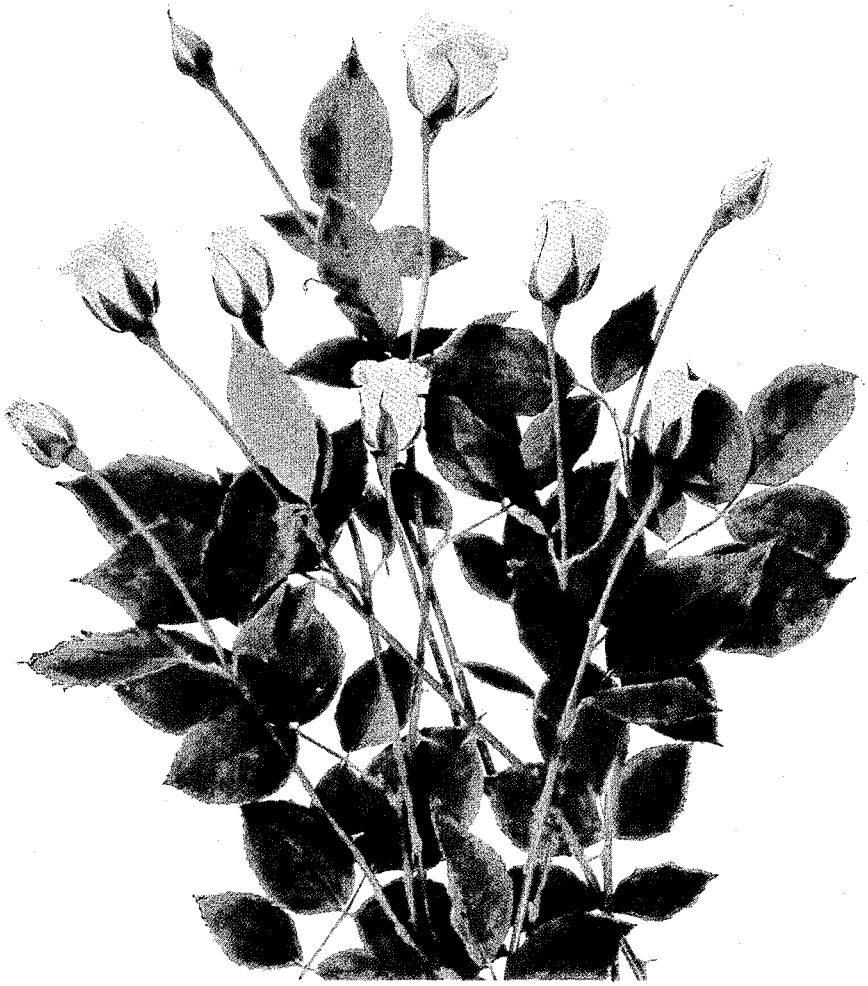
INVENTOR
R.L.Byrum
By Robbins Robb
ATTORNEYS Patented May 19, 1942

Plant Pat. 517

UNITED STATES PATENT OFFICE

517

ROSE PLANT

Roy L. Byrum, Richmond, Ind., assignor to Joseph H. Hill Company, Richmond, Ind., a corporation of Indiana Application November 1, 1941, Serial No. 417,558

1 Claim. (Cl. 47—61)

The present invention relates to a new and distinct variety of miniature rose plant, originating from the crossing of "Joanna Hill" with an unnamed seedling, a large hybrid tea rose of a yellow color similar to that of the well-known variety "Souv. de Claudius Pernet."

It may be noted, by way of comparison, that the only yellow miniature (semi-miniature) hybrid tea rose of which I am aware, is my previous origination commercially known as "Yellow Dot" (Plant Patent No. 312). However, this new variety is smaller and does not otherwise resemble "Yellow Dot." It resembles more "Joanna Hill" in growth, but produces short stems, since it is a miniature, and the bloom is much smaller than "Joanna Hill." So far as color is concerned, the new rose resembles its pollen parent, but is much smaller in size. It is not a polyantha.

The particular value of this new variety resides in special adaptability for corsages, both on account of its miniature size and the color of its blooms, so popular for corsages.

Among other distinguishing features, I have observed that as this new rose opens on a rose plant in a greenhouse, the color gets lighter rapidly, becoming almost white, but when cut as a bud from a plant in the greenhouse and brought indoors, the color lightens very little, as it opens.

For geneological purposes, I note that the pollen parent used in originating this new variety was itself the result of a cross between "Justine" (Plant Patent No. 154) as the pollen parent, and "Captain Glisson" (Plant Patent No. 155) as the seed parent. It differs entirely from either of these varieties.

The following is a detail description of the new variety, the color terminology being in accord with Ridgway's Color Standard:

Type: Greenhouse; seedling; for cut flowers.

Class: Hybrid tea.

Breeding or discovery: Seedling.

*Seed parent.*—"Joanna Hill."

*Pollen parent.*—Unnamed seedling ("Justine"×"Captain Glisson").

Propagation: Holds its distinguishing characteristics through succeeding propagations by cuttings, grafting and budding.

*Flower*

Locality where grown: Richmond, Indiana.

Flowers borne: Singly to stem on strong, short stems.

Quantity of bloom: Abundant in greenhouse.

Continuity: Continuous.

Fragrance: Slight tea.

Bud:

*Peduncle.*—Medium length; slender; erect; stiff; medium green; almost smooth; few green hairs.

*Before calyx breaks.—Size*—small. *Form*—short; pointed, with a conspicuous neck; with foliaceous appendages on the surface of the bud; with slender, entire foliaceous parts extending beyond the tip of the bud equal to three-fourths or more of its length.

*As calyx breaks.—Color*—some buds are entirely Buff-Yellow, Plate IV; some are Light Orange-Yellow, Plate III, near tip.

*As first petal opens.—Size*—very small. *Form*—very short; pointed. *Color:* outside—some have Empire Yellow base, Plate IV, shading to Buff-Yellow, Plate IV; others are Empire Yellow, Plate IV, with a White edge toward tip of petal; inside—some petals are Apricot Yellow, Plate IV, while others are Light Orange-Yellow, Plate III. Opening—opens up well.

Bloom:

*Size, when fully open.*—Small; two inches to three inches.

*Petalage.*—Semi-double, from fifteen to twenty petals arranged irregularly.

*Form.*—Globular at first, becoming flat, open; petals remaining at first loosely rolled outward; becoming later, at maturity, loosely rolled outward.

Petals: Thick, with inside satiny and outside shiny.

*Shape.*—Outside—obovate, with apex flat with one notch—most with none. Intermediate—obovate, with apex flat with one notch—most with none. Inside—obovate; irregular with one notch—most with none.

This description of a newly opened flower was made from a rose grown in a greenhouse at Richmond, Indiana, in the month of August, 1941:

*Color.*—Outside petal: outside surface—Maize Yellow, Plate IV; tips White; inside surface—Pale Orange Yellow, Plate III; tips White. Intermediate petal: outside surface—Maize Yellow, Plate IV; inside surface—Pale Orange-Yellow, Plate III. Inner petal: outside surface—Maize Yellow, Plate IV; inside surface—Pale Orange-Yellow, Plate III.

*General color effect.*—Newly opened flower—Pale Orange-Yellow, Plate III. Three days open—Marguerite Yellow, Plate XXX.

*Behavior.*—Persist.

*Flower longevity.*—Cut roses grown in greenhouse kept at living room temperatures—six days in September.

This description was made from a rose that was open for three days in a greenhouse at Richmond, Indiana, in the month of September, 1941.

*Color.*—Outside petal: outside surface—Marguerite Yellow, Plate XXX; inside surface—Marguerite Yellow, Plate XXX. Inside petal: outside surface—Marguerite Yellow, Plate XXX; inside surface—Marguerite Yellow, Plate XXX.

*Reproductive organs*

Stamens: Medium number; arranged regularly about pistils.
Filaments: Long; reddish; most with anthers.
Anthers: Small; reddish; all open at once.
Pollen: Abundant; gold.
Pistils: Medium number.
Styles: Uneven; short; medium heavy; bunched.
Stigma: White.
Ovaries: Some protruding from calyx.
Hips: None.
Sepals: Permanent; spear-shaped.

*Color.*—Inside—Chalcedony Yellow, Plate XVII, center, edged by Biscay Green, Plate XVII. Outside—Light Bice Green, Plate XVII.

Seeds: None.

*Plant*

Foliage:

*Leaves.*—Compound of five leaflets; abundant; small; moderately leathery.

*Leaflets.*—*Shape*—ovoid, with apex acute; base obtuse; margin simply serrate. *Color*—mature: upper surface—Darker than Dark Dull Yellow-Green, Plate XXXII; under surface—Deep Dull Yellow Green (1) Plate XXXII, overlaid with Sage Green, Plate XLVII. *Young*: upper surface—Green with Bronze edges; under surface—Green overlaid with bronze.

*Rachis (the supporting stem of the compound leaf).*—Medium heavy; upper side, smooth, grooved; under side, prickly.

*Stipules.*—Medium long; medium wide; with medium long points turning out at an angle of less than 45°.

*Disease.*—Resistant to mildew and blackspot.

Growth:

*Habit.*—Bush; upright; much branched.

*Growth.*—Vigorous.

*Canes.*—Light.

*Main stems.*—Dull green with streaks of rust. *Thorns*—several; medium long; hooked downward; with long, narrow base. *Prickles*—none. *Hairs*—none.

*Branches.*—Dull Green. *Thorns*—several; medium long; hooked downward; with long, narrow base. *Prickles*—none. *Hairs*—none.

*New shoots.*—Green Bronze. *Thorns*-several; medium long; straight; with short, narrow base. *Prickles*—none. *Hairs*—none.

I claim:

A new and distinct variety of hybrid tea rose plant, characterized as to novelty by its miniature size, the yellow coloring and abundance of its blooms, their lasting quality and general distinction from all other roses of its class, substantially as shown and described.

ROY L. BYRUM.